United States Patent [19]

Angelsen

[11] Patent Number: 5,195,519

[45] Date of Patent: * Mar. 23, 1993

[54] MINIATURIZED MECHANICALLY-STEERABLE ULTRASONIC PROBE

[76] Inventor: Bjorn A. J. Angelsen, Anders Tvereggens veg 34, 7037 Trondheim, Norway

[*] Notice: The portion of the term of this patent subsequent to Nov. 27, 2007 has been disclaimed.

[21] Appl. No.: 615,213

[22] Filed: Nov. 19, 1990

Related U.S. Application Data

[63] Continuation-in-part of Ser. No. 288,690, Dec. 22, 1988, Pat. No. 4,972,839.

[51] Int. Cl.⁵ .............................................. A61B 8/06
[52] U.S. Cl. ............................ 128/660.1; 128/662.06
[58] Field of Search .................. 128/660.09, 660.1, 661.08–661.10

[56] References Cited

U.S. PATENT DOCUMENTS

| | | | |
|---|---|---|---|
| 4,399,703 | 8/1983 | Matzuk | 128/660.1 |
| 4,509,526 | 4/1985 | Barnes et al. | 128/661.1 |
| 4,757,818 | 7/1988 | Angelsen | 128/661.08 X |
| 4,972,839 | 11/1990 | Angelsen | 128/662.06 |

Primary Examiner—Francis Jaworski
Attorney, Agent, or Firm—Cohen, Pontani, Lieberman & Pavane

[57] ABSTRACT

A miniaturized ultrasonic probe includes a housing encasing a motor, an ultrasonic transducer mounted for controlled rotation on the motor shaft, and an angular position sensor connected to the shaft. The housing has a radiating dome about the transducer and is sealed and wholly filled with an acoustically-transparent fluid. The transducer may be specially configured for use in continuous wave Doppler measurements of blood flow velocities and, for this purpose, may include a first portion for continuously transmitting an ultrasound beam and a second portion for continuously receiving backscattered ultrasound reflections of the transmitted ultrasound beam. The position sensor is implemented using a low mass variable-inductor arrangement. The resulting probe attains unusually rapid accelerations and changes in beam direction with highly accurate control of transducer orientation in a notably and advantageously miniaturized construction.

36 Claims, 8 Drawing Sheets

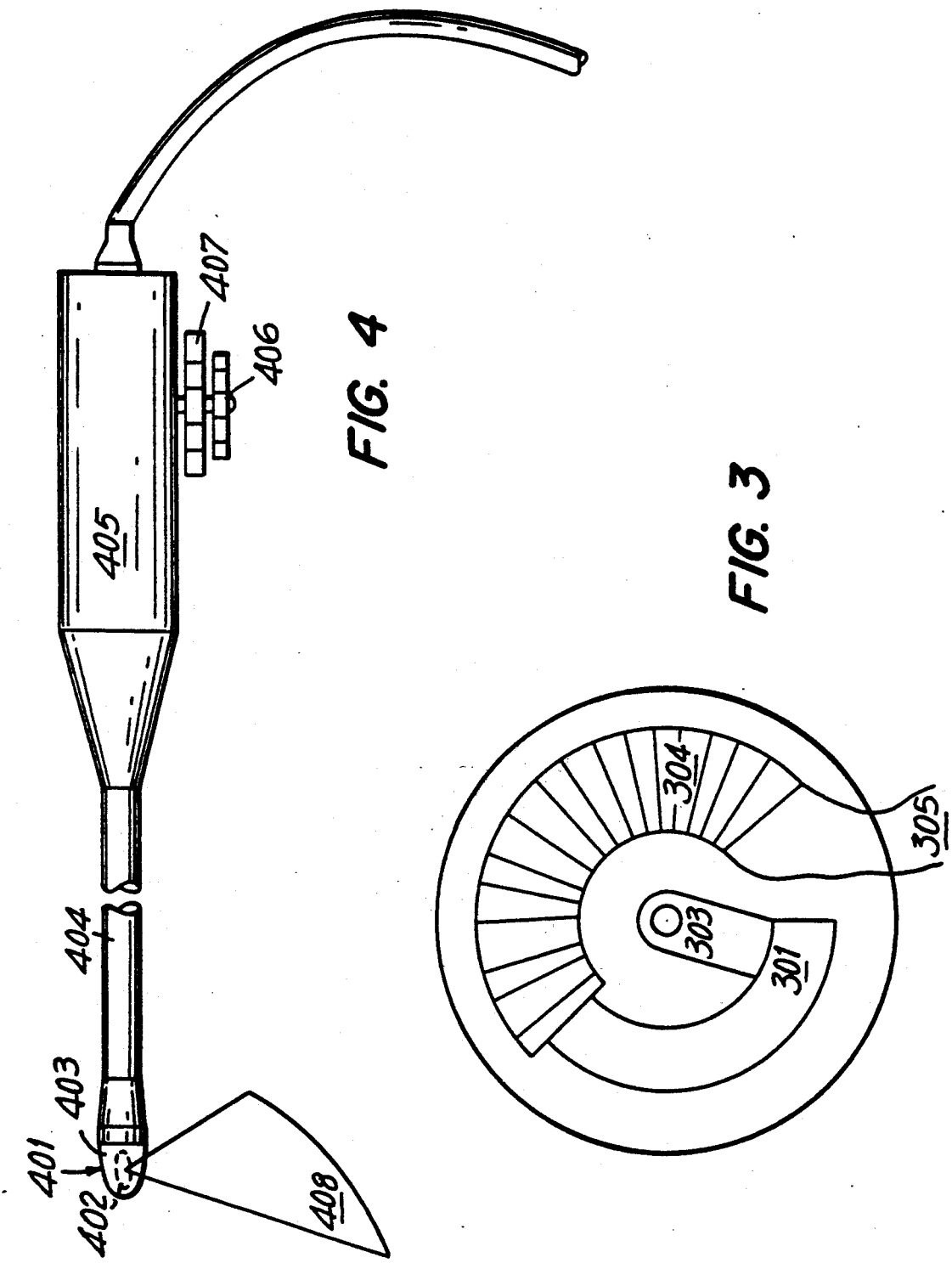

MINIATURIZED MECHANICALLY-STEERABLE ULTRASONIC PROBE

CROSS-REFERENCE TO RELATED APPLICATION

This is a continuation-in-part of copending U.S. patent application Ser. No. 288,690, filed Dec. 22, 1988 and now U.S. Pat. No. 4,972,839.

FIELD OF THE INVENTION

The present invention relates to ultrasonic probes and, in particular, to a miniaturized steerable ultrasonic probe for use in medical—such as intracavity and surgical—applications.

BACKGROUND OF THE INVENTION

Ultrasonic imaging advantageously enables real-time visualizing of structures within a human or animal body such, for example, as biological tissue, as well as the measurement and imaging of blood and other fluid flow velocities in internal body structures such as blood vessels and heart cavities. As heretofore practiced, a transducer is typically placed noninvasively on the skin or within a naturally-accessible internal cavity such as the esophagus, the vagina and the rectum. The ultrasonic beam is then scanned across the external or internal wall or skin or tissue surface to perform pulse echo reflection imaging of tissue structures in the skin or cavity wall and of structures adjacent to the cavity—e.g. the heart, spleen, prostate and uterus.

For intracavital applications, various kinds of arrays—such as switched linear or curvilinear array, and linear phase array types—have been employed. The use of annular arrays is particularly advantageous in such applications since they provide a circularly symmetrical dynamic focus and it is fairly simple to do continuous wave (CW) Doppler measurements of blood velocities using a steerable, albeit mechanically steerable, ultrasonic beam. In addition, because their individual elements are wider it is easier to fabricate such transducers for use at higher ultrasonic frequencies than with linear phased arrays. And annular arrays exhibit increased sensitivity for Doppler measurements and for imaging of blood velocities.

Phased and linear arrays, on the other hand, present problems in operating at relatively high ultrasonic frequencies—i.e. in the range of 7 to 10 MHz. They also provide electronically steered focusing only in the scan plane, the focus being fixed normal to that plane, whereas annular arrays provide improved lateral resolution normal to the scan plane.

Annular arrays, however, are disadvantageous in applications such as those contemplated for the present invention because they require that beam scanning be performed by mechanically or otherwise physically moving the transducer, as through a predetermined wobbling or rotative motion. This has proven particularly problematical in applications appropriate for or necessitating intracavital insertion of the probe since, for the highly miniaturized constructions necessary to accommodate their insertion into the body, prior art ultrasonic probes have been unable to attain sufficiently accurate control of the mechanical movement of the beam for these applications—especially where a wobbling motion of the beam is desireable or required. This deficiency has seriously hampered the fully effective use of ultrasonic probes during surgery—as, by way of example, for in situ observation of undissected structures such as tumors and atheroma in vessels, and for the measurement and imaging of blood velocities within vessels and cardiac cavities to provide both pre-procedure guidance for and ongoing control of surgical operations and evaluations.

OBJECTS OF THE INVENTION

It is accordingly the desideratum of the invention to provide a miniaturized ultrasonic probe enabling highly accurate steerability and control of its scannable ultrasonic beam. It is a particular object of the invention to provide such a probe of sufficiently small size for enabling effective intracavital use.

It is a further object of the invention to provide such a miniaturized probe in which the ultrasonic beam is mechanically steerable.

It is another object of the invention to provide such a probe for high resolution imaging at relatively high frequencies.

It is also an object of the invention to provide such a probe which is capable of projecting an ultrasonic beam at both high frequencies for high resolution imaging and at relatively lower frequencies for improved penetration and imaging of larger physical structures.

A further object of the invention is to provide such a probe in which the beam scanning arrangement is structurally and operationally optimized to provide extremely rapid accelerations of the beam and, therefore, of changes in the direction of beam movement, so as to enable time-shared two-dimensional imaging and Doppler measurement of, for example, blood velocities at a rate sufficient to approximate effective concurrency thereof.

Yet another object of the invention is to provide such a probe which provides a focused beam throughout the scanned range of interest, higher than 7 MHz operation, high sensitivity in flow imaging and Doppler measurement, and ease of use in carrying out steerable CW Doppler measurements.

A still further object of the invention is to provide such a probe which is capable of being readily held on one or between two fingers of a user's hand for controlled, accurate and convenient movement of the probe or probe head about a surgical field or otherwise within a patient's or subject's body.

Another object of the invention is to provide a miniaturized ultrasonic probe constructed and operable for continuous wave Doppler measurements of blood flow velocities.

Other objects and features of the present invention will become apparent from the following detailed description considered in conjunction with the accompanying drawing. It is to be understood, however, that the drawings are designed solely for purposes of illustration and not as a definition of the limits of the invention, for which reference should be made to the appended claims.

BRIEF DESCRIPTION OF THE DRAWING

In the drawing, wherein similar reference characters denote similar elements throughout the several views:

FIG. 1b illustrates the sandwich-like configuration of the transducer incorporated in the probe tip of FIG. 1a;

FIG. 3 is a sectional plan view of an angular position sensor incorporated in the probe tip of FIG. 1a;

FIG. 4 diagrammatically illustrates a miniaturized ultrasonic probe in accordance with a first embodiment of the invention and incorporating the probe tip of FIG. 1a;

FIG. 5 illustrates, in longitudinal cross-section, a modification of the probe tip of FIG. 1a;

DETAILED DESCRIPTION OF THE PREFERRED EMBODIMENTS

Figure 1A:
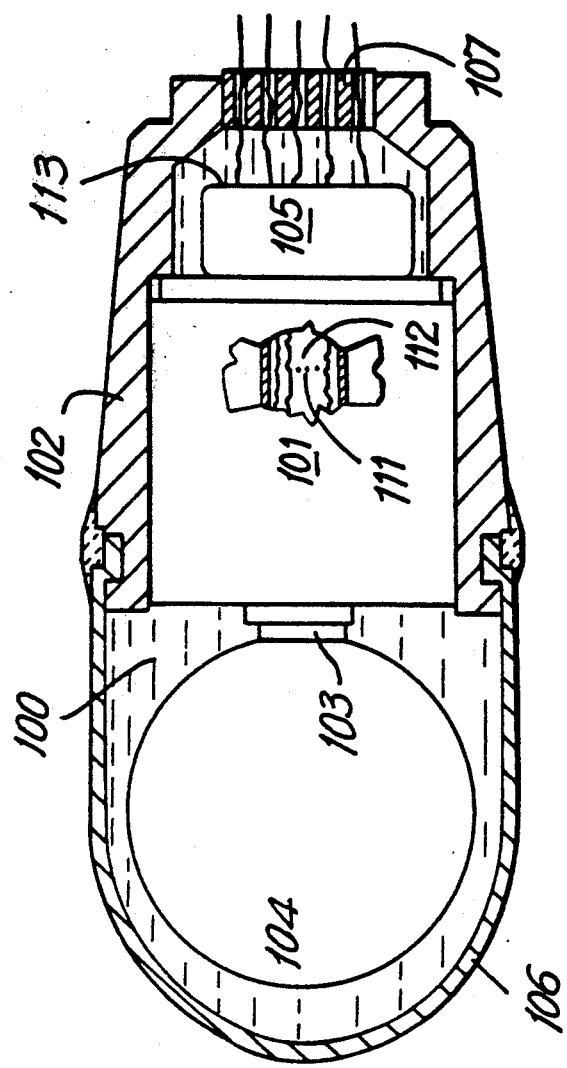
FIG. 1a is a simplified longitudinal cross-section of a first embodiment of a miniaturized ultrasonic probe tip having a mechanically-steerable ultrasonic beam and constructed in accordance with the present invention.

With initial reference to FIG. 4, there illustrated is a first embodiment of a miniaturized ultrasonic probe constructed in accordance with the present invention. The probe consists of a miniaturized probe tip 401 which includes, as hereinafter described in additional detail, a motor, an angular position sensor and a pivotable transducer 402 which is substantially surrounded by an acoustically transparent dome 403. The interior of dome 403 is preferably filled with an acoustically transparent fluid. The probe tip 401 is dependently carried on an arm or holder 404 and an attached handle 405 which may be appropriately configured for ready grasping in the hand of a user to facilitate insertion and maneuvering of at least the probe tip 401 in an interior human or animal body cavity or surgical site.

Arm 404 may be formed of a relatively stiff or rigid material for such applications as transvaginal and transrectal imaging, or it may be bendable or otherwise flexible as in a gastroscope for transesophageal imaging of the heart and aorta or of the gastro-intestinal tract. Where the arm 404 is flexibly implemented, remotely-controlled dynamic bending or reshaping of the arm so as to appropriately steer or direct the probe tip 401 into or through the body may be enabled by the provision of lines or wires, as is well known in connection with endo/gastroscopes. Such selectively controlled remote steering may, by way of example, be carried out through user operation of control wheels or knobs 406, 407 to provide dual-plane dynamic reshaping of flexible arm 404. As should be apparent to those skilled in the art, the acoustic transducer 402 is arranged for pivotal movement about the probe axis so as to operatively provide a scan plane or sector 408 of the ultrasonic beam.

Figure 1B:
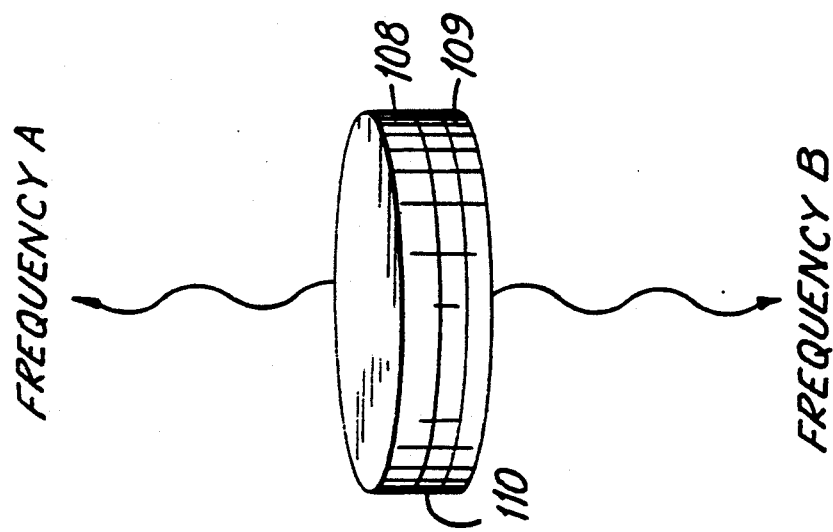

A particularly preferred, but not required, transducer construction for use in the miniaturized ultrasonic probe of the invention is depicted in FIG. 1b. As there shown, the transducer is in the form of a dual-frequency sandwich-like configuration assembled of a plurality of disc-shaped elements. More particularly, the transducer assembly is comprised of a first disc-shaped transducer 108, a second disc-shaped transducer 109 and a disc-shaped acoustically isolating material 110 interposed between and connecting the confrontingly opposite faces of the transducers 109, 110. The first transducer 108 is fabricated for operatively radiating at an ultrasonic frequency A from its face or surface opposite the acoustically isolating material 110, and the second transducer 109 similarly operatively radiates from its face opposite material 110 at a different ultrasonic frequency B. Thus, the transducer assembly is capable of operatively emitting different ultrasonic frequencies from its opposite faces with, as presently contemplated, one of the transducers selected at any particular time, as for example through the use of relays or other suitable control circuitry, and thereby connected to an associated ultrasonic scanner (not shown) or the like. Switching from the first to the second, or from the second to the first, transducer—as selected for example from the control panel of the scanner—thus requires that the dual-frequency probe be rotated 180 degrees about its longitudinal axis in order to scan the same target(s) within the scan sector.

The primary elements of the probe tip 401 of FIG. 4 are depicted in FIG. 1a. An electric motor 101 mounted within a motor cover or housing 102 is operable for rotating the motor shaft 103 which extends along the main or longitudinal axis of the probe. Motor 101 may optionally be constructed so that its shaft 103 is rotatable through only a predeterminately limited range of angular motion; alternatively, suitable limit stop members (not shown) or the like may be associated, in any appropriate manner, with the motor or motor shaft or other operatively movable probe element(s) for limiting the range of angular rotation of the transducer. In the illustrated and preferred form of the invention, the acoustic transducer assembly 104—such, for example, as that depicted in FIG. 1b—is mounted or otherwise secured directly to the shaft 103 so that the transducer 104 is carried through the same angular rotation as is the rotor or shaft of the motor 101. Also mounted or secured to the motor shaft is an angular position sensor 105 operable for following or determining the angular position or rotation of the rotor and ultrasonic transducer 104. The electrical connections to the sensor 105 and to the motor 101 are preferably, as is known in the art, connected in a servo-loop control arrangement for enabling accurately controlled steering of the angular position of the transducer. With this arrangement, the ultrasonic beam may be operatively steered or directed into and along a desired direction within the scan sector, or be caused to follow a particular predetermined sweep of one or a multiplicity of directions under the control of the user.

Of course, as should also be apparent the direct mounting of the transducer assembly 104 to the motor shaft 103 may be modified by the provision of an appropriate gearing arrangement or the like interposed between the transducer and shaft, with the construction of sensor 105 correspondingly modified to enable the sensor to provide a signal directly dependent on the angular orientation of the transducer 104. However, direct mounting of the transducer assembly 104 to the motor shaft 103 is preferred because it significantly reduces the mass of moving parts in the probe tip and thereby enables attainment of the unusually rapid accelerations and changes in beam direction, without sacrificing highly accurate mechanically-driven control of the movable transducer, which are a fundamental feature and advantage of the miniaturized ultrasonic probe of the invention.

The whole of the probe tip is incorporated within a hermetically or otherwise sealed cover or casing comprised of the acoustic dome 106, fabricated of an ultrasonically transparent material, and the motor housing 102. Preferably, the entire probe tip is filled with an acoustically transparent fluid 100 so that the transducer assembly 104, motor 101 and position sensor 105 are fully immersed in the fluid. This arrangement obviates the need to incorporate dynamic fluid seals about the motor shaft, thereby avoiding the introduction of frictional forces between the shaft and such fluid seals and minimizing the effective mass of moving parts in the probe tip. Omission of dynamic fluid seals about the motor shaft also eliminates problems which commonly develop as a result of fluid leakage through or about such seals.

The wires or leads representing the electrical connections to the transducer 104, motor 101 and position sensor 105 exit the probe tip through a rear cover 107 for connection to the imaging system or apparatus to which the miniaturized ultrasonic probe of the invention is operatively connected in any appropriate manner. The electrical connections to the wobbling or otherwise movable transducer and to the motor may, for example, be conveniently implemented using so-called flying leads. In order to reduce bending or kinking, and corresponding damage to or breakage, of the wires which connect to the transducer 104 and motor 101, these wires 112 may advantageously be fed through the hollow interior 111 of the motor shaft, exiting the shaft at its rearwardly-disposed end 113 and being then directed through the rear cover 107 of the probe tip. This arrangement leaves both beam radiating faces of the transducer disc assembly free for unimpeded acoustic transmission, and the interface at the end 113 of the hollow shaft permits only minimum bending of the wires with wobbling or other rotative motion of the motor shaft and transducer assembly.

Figure 2A:
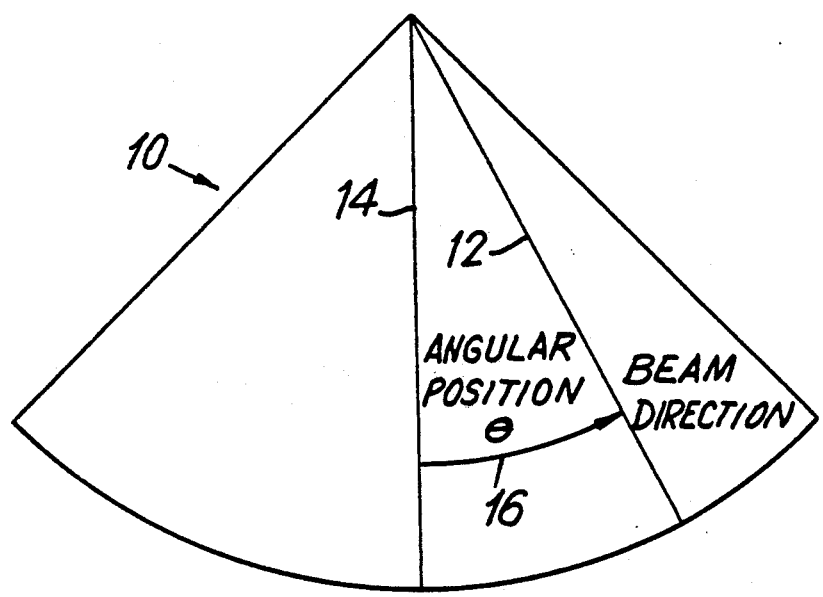
FIGS. 2a and 2b diagrammatically and graphically illustrate, by way of example, a periodic series of angular sweeps of an ultrasonic transducer with rapid jumps in beam direction enabling combined tissue imaging, flow imaging and blood velocity measurements.
Figure 2B:
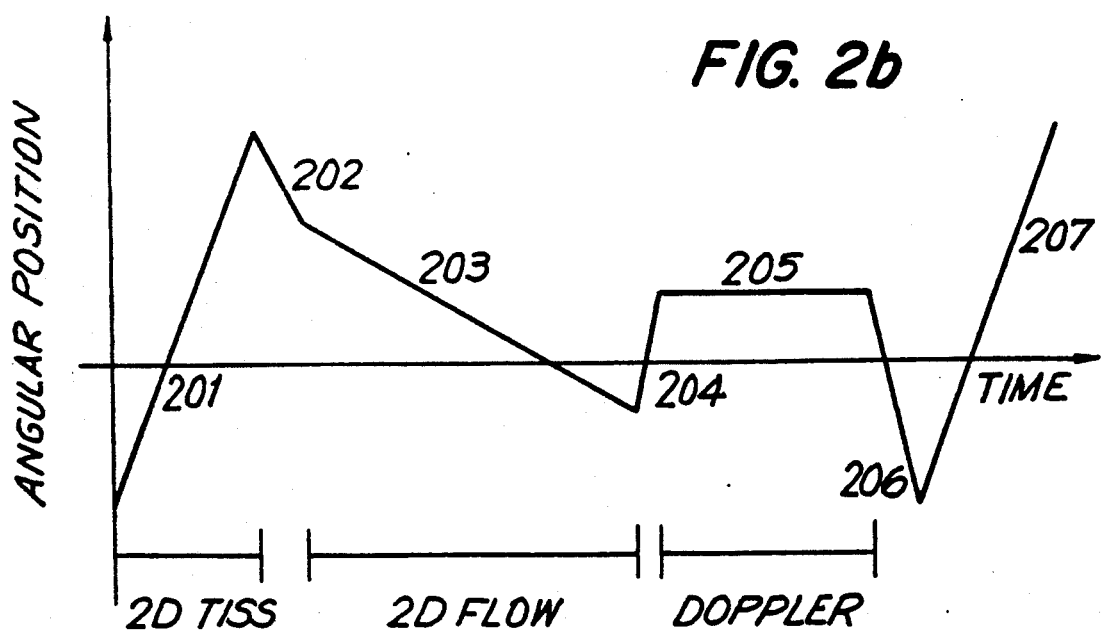

FIG. 2a illustrates a typical sector 10 of a plane within which an ultrasonic transducer beam emitted from the miniaturized probe of the invention is operatively sweeping. The shaded line 12 indicates the then current beam direction; the angular position of the beam is measured from the sector center line 14 to the current beam direction 12, as indicated by the arrow 16. FIG. 2b charts the changing angular position of an ultrasonic beam over a particular time interval as the beam is swept within the sector 10 through a periodic or repeatable, by way of example, series of directional sweeps illustrated solely for convenience of description. Thus, the sweep segments illustrated in FIG. 1b begin with a first, fairly rapid sector sweep 201 of the beam for performing tissue imaging, followed by a rapid change 202 of beam direction preparatory to a second, relatively slower sweep 203 commencing at a decreased angular position for performing flow imaging. This is then followed by a further rapid change 204 of beam direction to a stationary beam angular position 205 for performing either pulsed or continuous wave Doppler measurements, and a third rapid change 206 of beam direction to a predetermined angular position for initiating a new series or sequence of, for example, a similar group of angular sweeps, commencing with a first rapid sector sweep 207 for performing tissue imaging.

It is important to the currently contemplated medical applications of the miniaturized ultrasonic probe of the present invention that the changes 202, 204, 206 of beam direction be carried out with sufficient rapidity so that different measurements—i.e. tissue imaging, flow velocity imaging and Doppler blood velocity measurements—are performed so closely together in time as to appear substantially simultaneous or concurrent to the user as, for example, in accordance with the time-sharing method disclosed in U.S. Pat. No. 4,559,952 titled Method of Ultrasonically Measuring Blood Velocity. As a consequence, the design of the miniaturized ultrasonic probe of the invention is optimized to provide for unusually rapid acceleration of the beam direction and to thus minimize switching time between its anticipated modes of operation. As herein disclosed, the inventive probe design accordingly incorporates minimization of moving parts, of the mass of moving parts and of the forces that must be overcome to move those parts. These intentions are implemented, for example, through mounting of the transducer directly to the motor shaft. It is further preferred, in this regard, that the motor employ a rotor formed of a self-supported winding containing no iron and, in addition, that the probe include a low-mass position sensor such, for example, as that illustrated in FIG. 3 and hereinafter described. The present design also realizes unusually rapid accelerations of beam direction by omitting the use of dynamic fluid seals on or about the motor shaft—by reason of the disposition of the motor, position sensor and transducer in a fluid-filled chamber—thus eliminating friction from such seals that would otherwise interfere with the operative movement and accelerations of the ultrasonic beam.

A currently preferred form of angular position sensor 105 is depicted in FIG. 3. A ferrite member 301 in the form of an arcuate or generally circular toroid is connected to the motor shaft 302 by a radially-oriented arm 303. Thus, as the motor shaft is operatively rotated, it carries the ferrite member 301 correspondingly and increasingly into or out of the interior of a circularly-wound coil 304. The inductance of coil 304 consequently depends on how far the ferrite member 301 extends into the interior of the coil, the inductance thereby providing an indication of the relative angular position, and of changes in said angular position, of the motor shaft 302 and of the directly-connected transducer assembly.

In addition to its structural simplicity and resulting operative reliability, the position sensor of FIG. 3 is advantageous in that only two electrical lead or wire connections 305 are needed for discerning the angular position, or changes in the angular position, of the motor coil and, therefore, of the ultrasonic beam direction. Those skilled in the art will of course recognize that the FIG. 3 position sensor may be readily modified, as a matter of design choice, for example by mounting the coil 304 to the shaft-depending arm 303, and maintaining the ferrite member 301 stationary as the coil operatively moves over and about the stationary ferrite member.

Figure 5:
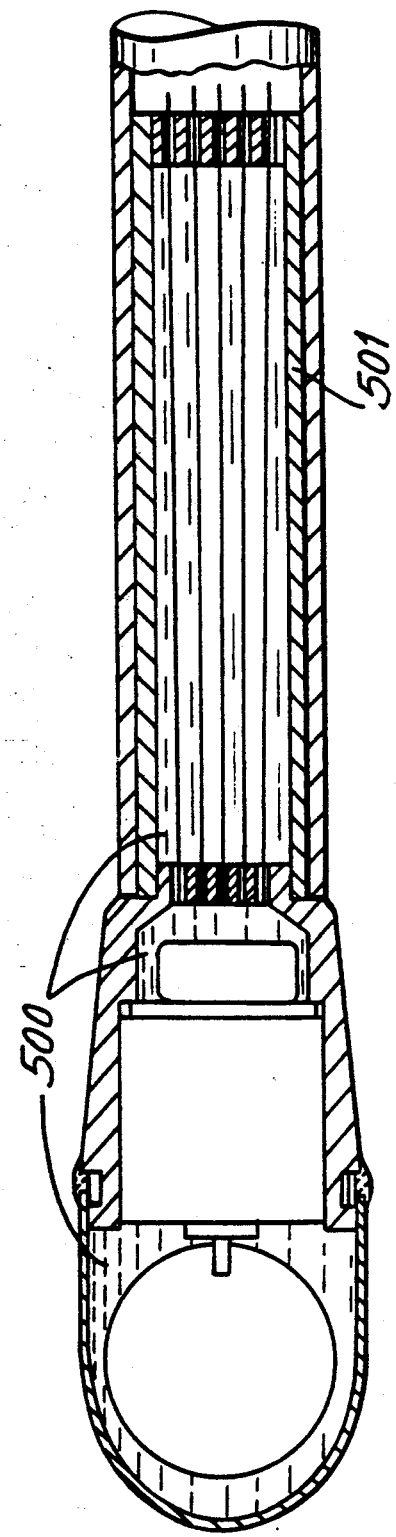

Because the probe tip casing is hermetically or otherwise sealed, it is advantageous and preferred to provide means for accommodating relative changes—resulting for example from temperature-induced expansion and contraction—in the volume of the acoustically transparent fluid filling the sealed interior of the probe tip. Such volumetric changes can be accommodated by incorporating a flexible region in the probe tip casing wall or, as illustrated in FIG. 5, by extending the rear end of the probe tip casing with a flexible or elastic tube 501. The flexible tube 501 may, for example, be mounted in the tip of a gastroscope or the like and, by reason of its flexibility, will neither increase the length of the nonflexible forward portion of the probe nor have any practical effect on the flexibility of the gastroscope tip. In the FIG. 5 modification, the acoustic fluid 500 fills the entirety of the illustrated probe structure.

Figure 6:
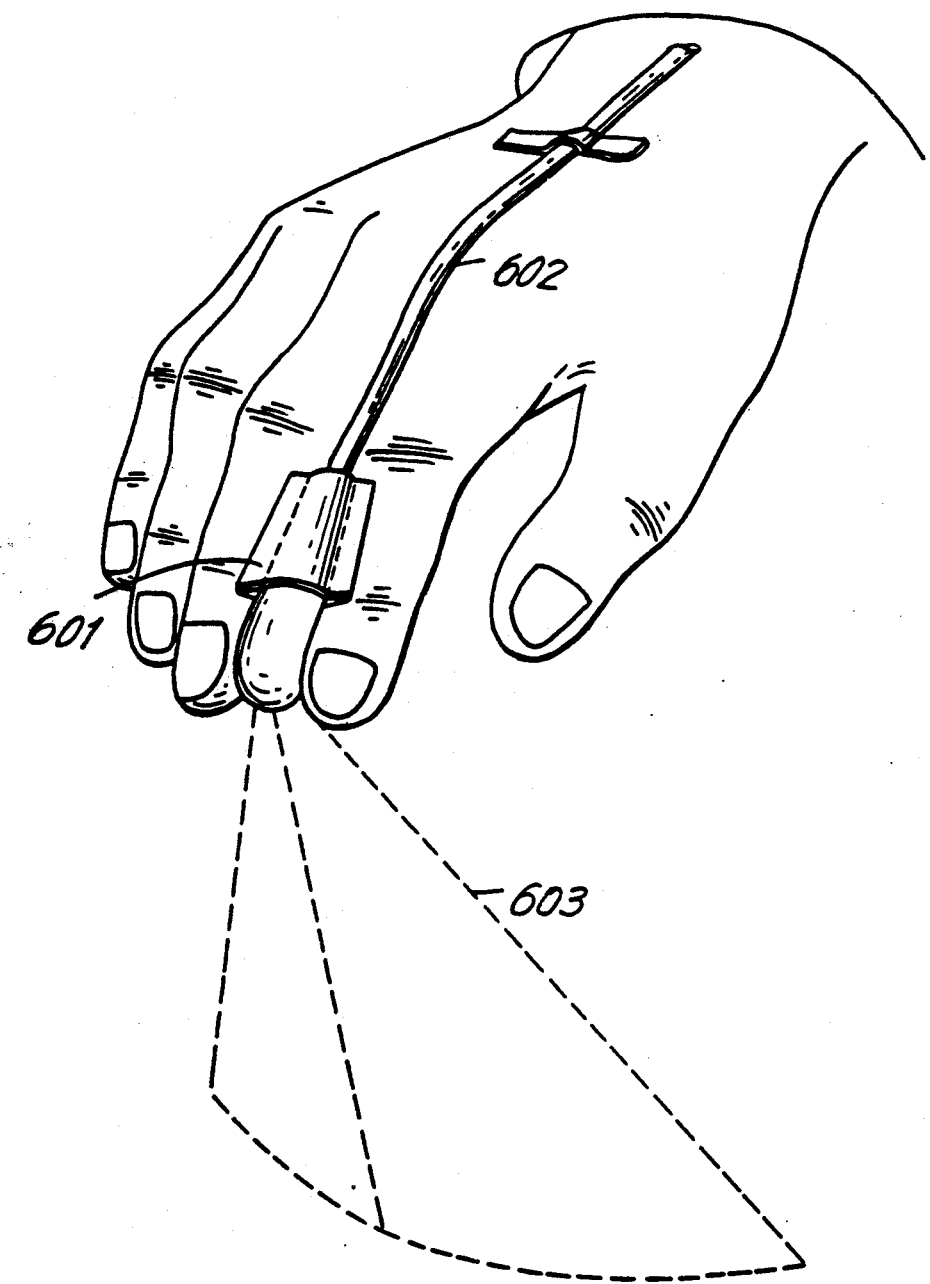
FIG. 6 is an elevated perspective view of a user's hand holding a miniaturized ultrasonic probe in accordance with a further embodiment of the invention.
Figure 7A:
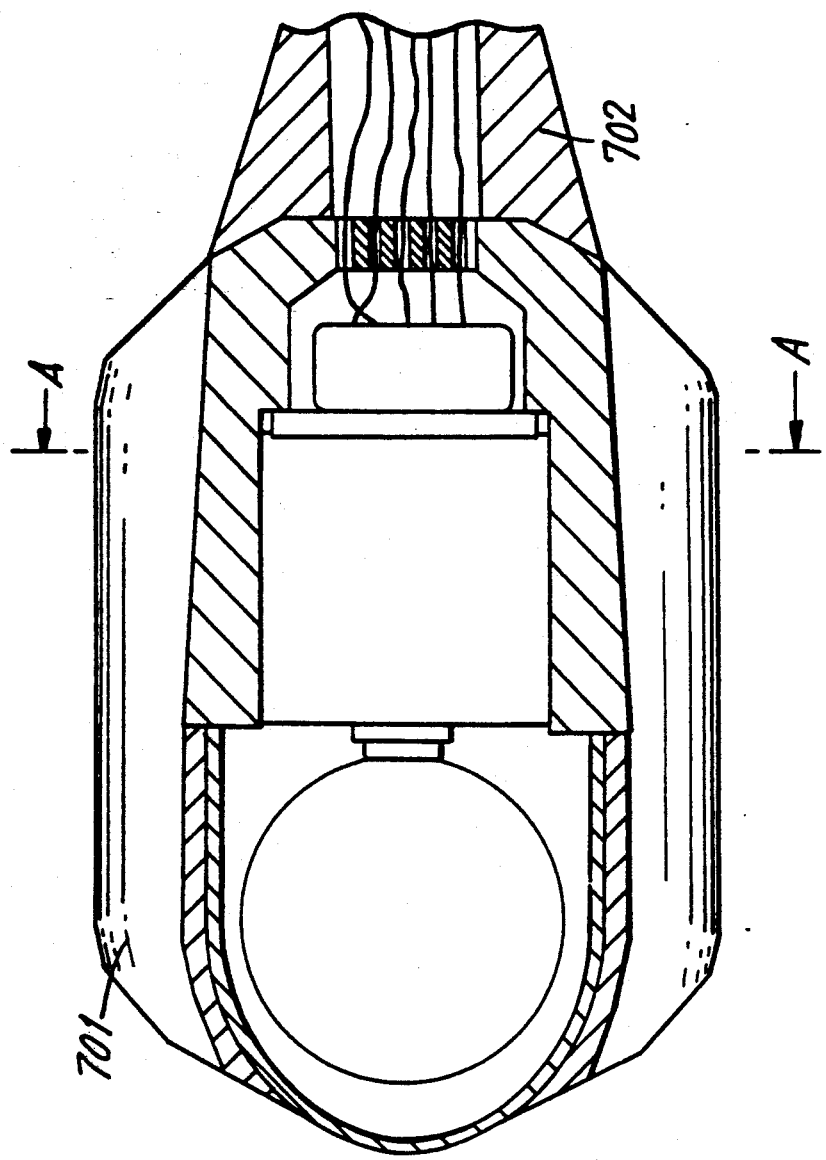
FIGS. 7a and 7b illustrate, in simplified longitudinal cross-section, the miniaturized ultrasonic probe of FIG. 6.
Figure 7B:
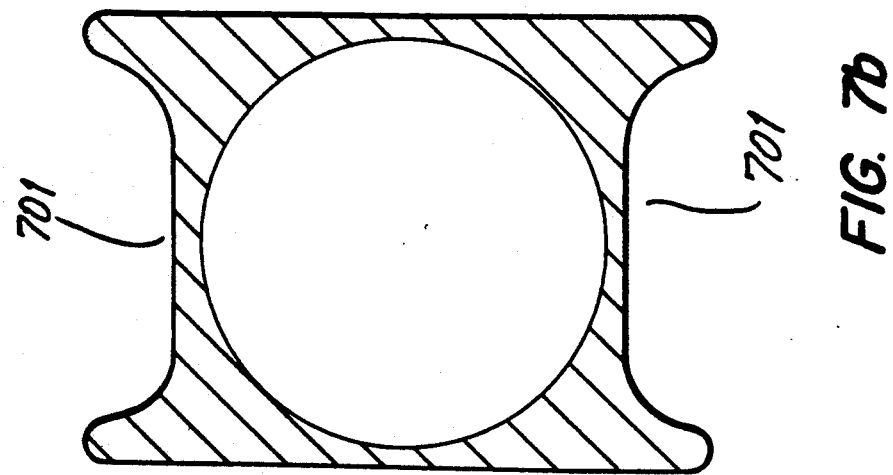
Figure 8:
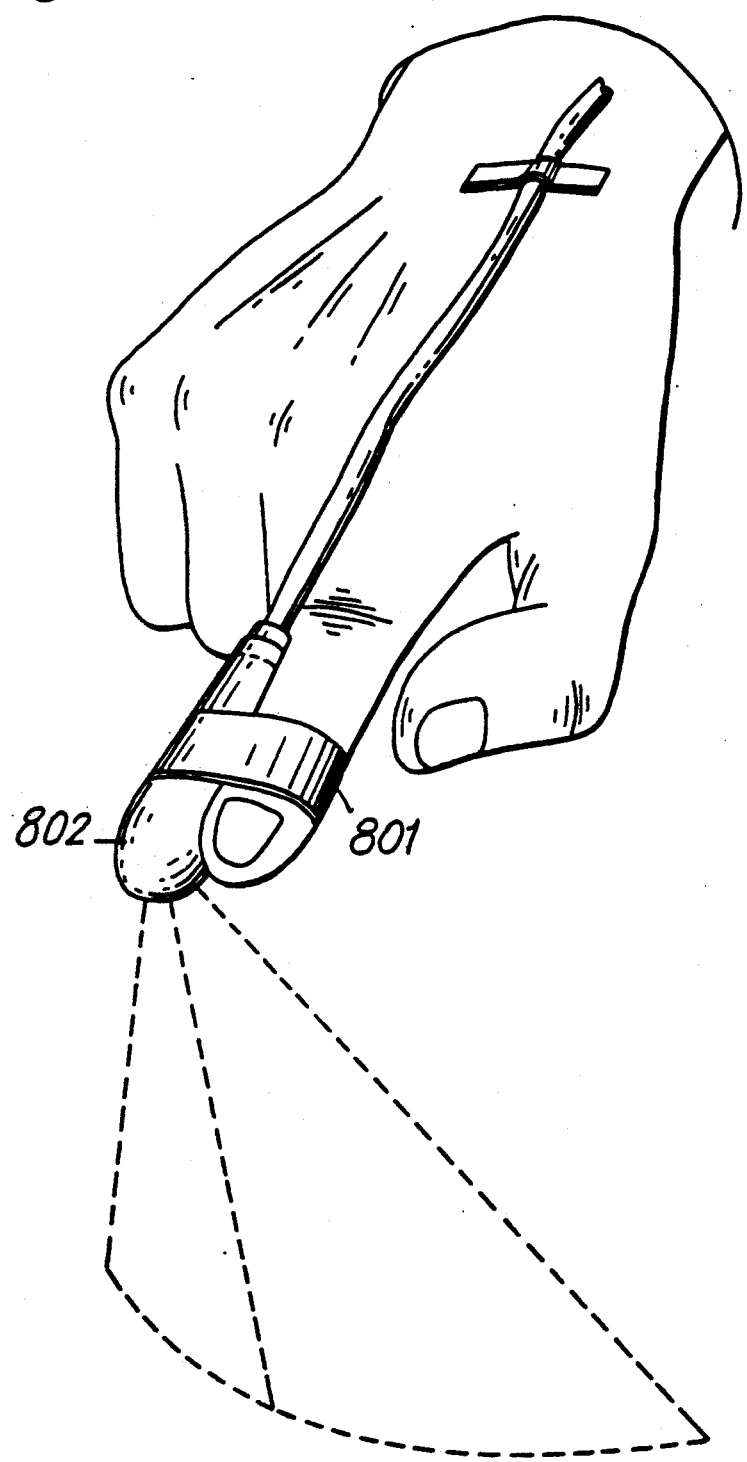
FIG. 8 is an elevated perspective view of a modified arrangement for holding the probe of FIGS. 6 and 7a,b on a user's hand.

A further embodiment of a miniaturized ultrasonic probe in accordance with the invention and configured for particularly advantageous use in surgical applications is shown in FIGS. 6 to 8. In this second embodiment, the moving or operating elements of the probe may be, and preferably are, substantially as disclosed with respect to the first embodiment heretofore described. In this case, however, the transducer, drive motor and angular position sensor are encased in a combined cover and grip system 401 (FIG. 6) especially adapted for ready retention between two adjacent fingers or fingertips of a user's hand. This arrangement enables easily and conveniently controlled movement of the probe under the fingertip control of the user about a surgical field without interfering with the surgeon's or operator's view of the field. The electrical cable 602 connecting the miniaturized probe to the associated driving and/or imaging apparatus (not shown) may be taped atop or otherwise led along the user's hand and/or wrist as appropriate, thereby avoiding interference with the typical sectorial scanfield 603 of the ultrasonic beam emitted by the probe.

A preferred configuration of the combined cover and grip system 601 for retaining the miniaturized probe between two adjacent fingertips is seen in further detail in FIGS. 7a and 7b. Substantially concave or otherwise suitably curved finger grip surfaces 701 are defined in the outer cover of the probe casing; the transducer assembly, motor and angular position sensor are as heretofore described in connection with the first embodiment of the invention illustrated in FIGS. 1a, 1b and 3. A sheath 702 provides a streamlined flexible connection between the transducer housing and the rearwardly-extending electrical cable 602. The transducer casing or housing may also advantageously incorporate a flexible or elastic portion, such as the rearwardly-disposed and extending tube 501 (FIG. 5) of the first embodiment of the invention, for accommodating volumetric changes in the acoustic fluid filling the sealed interior of the probe tip.

A modified grip system, also enabling fingertip control of the position and location of the probe, is depicted in FIG. 8. This modified grip system includes a band-like retainer 801, fabricated for example of an elastic material, dependingly secured to or releasably engageable with the exterior casing of the probe 802. This arrangement permits accurate and convenient positional control and movement of the probe in and about the surgical field through user manipulation of a single finger or fingertip.

Figure 9A:
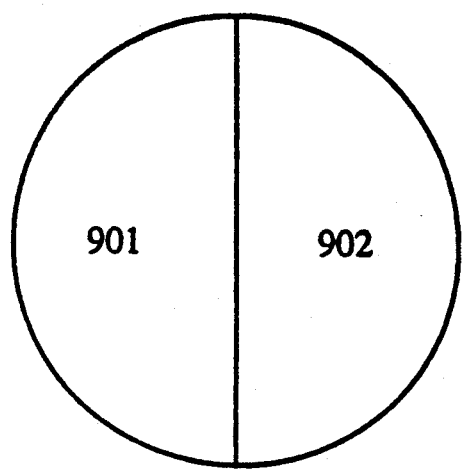
FIGS. 9a and 9b are top plan views of two embodiments of ultrasound transducers for use in the miniaturized probe of the invention in carrying out continuous wave Doppler measurements of blood flow velocities.
Figure 9B:
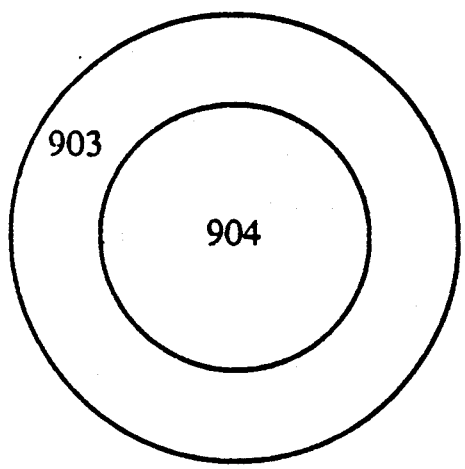

FIGS. 9a and 9b depict embodiments of an ultrasound transducer specially constructed for use in continuous wave (CW) Doppler measurements of blood flow velocities. For this purpose, these transducers are split or divided into two distinct parts, one for the continuous transmission of ultrasound and the other for the continuous reception of backscattered reflections of the transmitted ultrasound wave. In the embodiment of FIG. 9a, for example, the circular transducer surface is split or divided into two integral halves 901, 902, the former providing an ultrasound continuous transmission portion and the latter an ultrasound continuous receiving portion. Similarly, the FIG. 9b embodiment is integrally formed of a generally annular outer ring 903 for continuous ultrasound transmission therefrom and which surrounds and bounds a centrally interior portion or central disk 904 for continuous ultrasound reception. Those skilled in the art will, of course, recognize that assignment of the ultrasound transmitting and receiving functions between the two integral transducer parts in each of FIGS. 9a and 9b may, alternatively, be the reverse of that mentioned above—i.e. that the transducer half 901 may be operated for ultrasound continuous reception while the half 902 is operated for ultrasound continuous transmission in FIG. 9a and, similarly, that the outer ring 903 in FIG. 9b may be used for continuous ultrasound reception and the central disk 904 for continuous ultrasound transmission.

The effective splitting or division of the ultrasound transducer into two discrete parts, one for continuous transmission of ultrasound and the other for continuous reception of reflections thereof, in accordance with FIG. 9b to define a discrete outer ring and an inner or central disk arrangement for carrying out CW Doppler measurements may also be advantageously implemented in conjunction with conventional annular transducer arrays. Such annular arrays, which are typically used for general ultrasound imaging with steered focus, are formed of a central disk surrounded by a plurality of annular rings, such for example as one central disk and seven concentrically-surrounding annular rings. By actuating the central disk and the surounding annular rings sequentially—as from the outer ring to the inner central disk—the outbound ultrasound wavefront can be curved and selected directional focussing of the ultrasound wave can be achieved. In accordance with the present invention, such an annular array can be employed for CW Doppler measurements by using, for example, the four outer rings of the array for simultaneous continuous transmission of ultrasound and the three inner rings and central disk for simultaneous continuous receipt of reflected ultrasound. This accordingly provides, using a conventional annular transducer array, a CW Doppler transducer structure that is, in effect, functionally equivalent in use to the transducer illustrated in FIG. 9b.

While there have been shown and described and pointed out fundamental novel features of the invention as applied to preferred embodiments thereof, it will be understood that various omissions and substitutions and changes in the form and details of the devices illustrated and in their operation may be made by those skilled in the art without departing from the spirit of the invention. It is the intention, therefore, to be limited only as indicated by the scope of the claims appended hereto.

What is claimed is:

1. A miniaturized ultrasonic probe, comprising:
   ultrasonic transducer means for emitting and receiving ultrasound waves for continuous wave Doppler measurements of blood velocity, said ultrasonic transducer means comprising a first part operable for continuously transmitting an ultrasound beam along a direction and a second part operable for continuously receiving backscattered ultrasound reflections from said transmitted ultrasound beam;

a motor having a shaft and operable for rotating said shaft, said transducer means being connected to said shaft for selective rotation of said transducer means with said shaft to selectively orient the ultrasound beam emitted by said transducer means first part;

sensor means connected to said motor shaft for providing a signal indicative of the angular position of said shaft and said transducer means so as to enable controlled steering of said transducer means for selectively varying the beam direction;

a substantially sealed housing encasing said transducer means, said motor and said sensor means, said housing comprising a dome of ultrasonically transparent material disposed about said transducer means and within which said transducer means is noninterferingly movable with operative rotation of said shaft; and an ultrasonically transparent fluid filling said substantially sealed housing so that the ultrasound beam emitted by said transducer means is radiated outwardly from said probe through said fluid and said housing dome along a direction which, with selective operation of said motor, is selectively variable through at least a portion of a scan sector.

2. A miniaturized ultrasonic probe in accordance with claim 1, wherein said transducer means is mounted directly to said motor shaft.

3. A miniaturized ultrasonic probe in accordance with claim 1, further comprising electrical leads connected to said transducer means, and wherein said motor shaft is hollow for protectively accommodating therein said electrical leads which extend therethrough and thereby preventing damage to said leads with rotative movement of said motor shaft and transducer means.

4. A miniaturized ultrasonic probe in accordance with claim 1, wherein said sensor means comprises a magnetic material and a coil, one of said magnetic material and coil being connected to said motor shaft for movement with operative rotation of said shaft into inductance-varying relation with the other of said magnetic material and coil so that the inductance of said coil varies with said motor shaft rotation and, correspondingly, with the rotative position of said transducer means.

5. A miniaturized ultrasonic probe in accordance with claim 1, wherein said housing further comprises a flexible portion for accommodating volumetric changes in said fluid.

6. A miniaturized ultrasonic probe in accordance with claim 5, wherein said flexible portion comprises a flexible tubular part disposed remote from said housing dome.

7. A miniaturized ultrasonic probe in accordance with claim 1, further comprising a flexible arm, and wherein said housing is mounted on said flexible arm and defines the tip thereof.

8. A miniaturized ultrasonic probe in accordance with claim 7, wherein said flexible arm contains said ultrasonically transparent fluid and includes a flexible portion deformable for accomodating volumetric changes in said fluid.

9. A miniaturized ultrasonic probe in accordance with claim 7, wherein said flexible arm has an initial shape, further comprising steering means operable for selectively changing the initial shape of said arm.

10. A miniaturized ultrasonic probe in accordance with claim 1, wherein said housing comprises exterior means for releasably engaging a user's finger with said probe so as to enable ready user manipulation of the probe.

11. A miniaturized ultrasonic probe in accordance with claim 10, said exterior means comprising a pair of oppositely disposed recesses, each said recess being configured for concurrently receiving a user's finger so that said probe is releasably retainable between a user's two fingers which are received in said respective recesses with the two fingers disposed in substantially parallel relation and separated by the interposed housing.

12. A miniaturized ultrasonic probe in accordance with claim 10, said exterior means comprising band means for releasably receiving a user's finger in encircling relation thereabout.

13. A miniaturized ultrasonic probe in accordance with claim 10, said exterior means comprising means for releasably retaining said probe between two of a user's adjacently-disposed fingers.

14. A miniaturized ultrasonic probe, comprising:
ultrasonic transducer means for emitting an ultrasonic beam along a first direction;

a motor having a shaft and operable for rotating said shaft, said transducer means being connected to said shaft for selective rotation of said transducer means with said shaft to selectively orient the ultrasonic beam emitted by said transducer means;

sensor means connected to said motor shaft for providing a signal indicative of the angular position of said shaft and said transducer means so as to enable controlled steering of said transducer means for selectively varying the beam direction, said sensor means comprising a coil defining therethrough an arcuate passageway and a correspondingly arcuate member, one of said coil and member being connected to said motor shaft for movement with rotation of the motor shaft relative to the other of said coil and member so that, as the motor shaft is operatively rotated, the arcuate member moves variably through and along the arcuate coil passageway to vary the coil inductance in a predetermined relationship to the rotative position of said transducer means and thereby provide a signal indicative of the angular position of the transducer means;

a substantially sealed housing encasing said transducer means, said motor and said sensor means, said housing comprising a dome of ultrasonically transparent material disposed about said transducer means and within which said transducer means is noninterferingly movable with operative rotation of said shaft; and an ultrasonically transparent fluid filling said substantially sealed housing so that the ultrasonic beam emitted by said transducer means is radiated outwardly from said probe through said fluid and said housing dome along a first direction which, with selective operation of said motor, is selectively variable through at least a portion of a scan sector.

15. A miniaturized ultrasonic probe in accordance with claim 14, wherein said transducer means is mounted directly to said motor shaft.

16. A miniaturized ultrasonic probe in accordance with claim 14, wherein said transducer means comprises a first transducer for emitting an ultrasonic beam in a first direction and a second transducer for emitting an ultrasonic beam in a second direction.

17. A miniaturized ultrasonic probe in accordance with claim 16, wherein said transducer means further comprises a sandwich-like structure in which said first and second transducers are mounted in back-to-back relation for emitting said ultrasonic beams in respectively opposite directions.

18. A miniaturized ultrasonic probe in accordance with claim 16, wherein said first and second transducers are individually operable and each of said transducers operably emits an ultrasonic beam at a different frequency so as to provide multifrequency operation of said probe.

19. A miniaturized ultrasonic probe in accordance with claim 16, wherein said first and second transducers are connected by an intermediate acoustic isolating material.

20. A miniaturized ultrasonic probe in accordance with claim 16, wherein said first and second transducers are configured as disks and are connected in back-to-back relation so as to emit said ultrasonic beams in respectively opposite directions.

21. A miniaturized ultrasonic probe in accordance with claim 16, wherein said first and second transducers emit said ultrasonic beams in respectively opposite directions.

22. A miniaturized ultrasonic probe in accordance with claim 14, further comprising electrical leads connected to said transducer means, and wherein said motor shaft is hollow for accommodating therethrough said electrical leads and thereby preventing damage to said leads with rotative movement of said motor shaft and transducer means.

23. A miniaturized ultrasonic probe in accordance with claim 14, wherein said housing further comprises a flexible portion for accommodating volumetric changes in said fluid.

24. A miniaturized ultrasonic probe in accordance with claim 23, wherein said flexible portion comprises a flexible tubular part disposed remote from said housing dome.

25. A miniaturized ultrasonic probe in accordance with claim 14, further comprising a flexible arm, and wherein said housing is mounted on said flexible arm and defines the tip thereof.

26. A miniaturized ultrasonic probe in accordance with claim 25, wherein said flexible arm contains said ultrasonically transparent fluid and includes a flexible portion deformable for accomodating volumetric changes in said fluid.

27. A miniaturized ultrasonic probe in accordance with claim 25, wherein said flexible arm has an initial shape, further comprising steering means operable for selectively changing the initial shape of said arm.

28. A miniaturized ultrasonic probe in accordance with claim 14, wherein said housing comprises exterior means for releasably engaging said probe with a user's finger so as to enable ready user manipulation of the probe.

29. A miniaturized ultrasonic probe in accordance with claim 28, said exterior means comprising a pair of oppositely disposed recesses, each adapted for receiving a user's finger.

30. A miniaturized ultrasonic probe in accordance with claim 28, said exterior means comprising band means for releasably receiving a user's finger.

31. A miniaturized ultrasonic probe in accordance with claim 28, said external means comprising means for releasably retaining said probe between two of a user's adjacently-disposed fingers.

32. A miniaturized ultrasonic probe in accordance with claim 14, wherein said arcuate member comprises an arcuate magnetic member.

33. A miniaturized ultrasonic probe in accordance with claim 14, wherein said arcuate member comprises an arcuate member of ferrite material.

34. A miniaturized ultrasonic probe in accordance with claim 14, wherein said arcuate member is connected to said motor shaft for movement with rotation of said shaft relative to said coil.

35. A miniaturized ultrasonic probe in accordance with claim 14, wherein said arcuate member and said coil are oriented substantially perpendicular to said motor shaft.

36. A miniaturized ultrasonic probe in accordance with claim 35, wherein said arcuate member is connected to said motor shaft for movement with rotation of said shaft relative to said coil.

* * * * *